US00PP36147P2

(12) United States Plant Patent
Danziger

(10) Patent No.: US PP36,147 P2
(45) Date of Patent: Sep. 24, 2024

(54) ***IMPATIENS* PLANT NAMED 'DNGISLPROR'**

(50) Latin Name: *Impatiens hawkeri*
Varietal Denomination: DNGISLPROR

(71) Applicant: Danziger 'DAN' Flower Farm, Beit Dagan (IL)

(72) Inventor: Gavriel Danziger, Beit Dagan, IL (US)

(73) Assignee: Danziger "DAN" Flower Farm (IL)

( * ) Notice: Subject to any disclaimer, the term of this patent is extended or adjusted under 35 U.S.C. 154(b) by 0 days.

(21) Appl. No.: 18/408,796

(22) Filed: Jan. 10, 2024

(51) Int. Cl.
*A01H 5/02* (2018.01)
*A01H 6/16* (2018.01)

(52) U.S. Cl.
USPC ..... Plt./318.6
CPC ..... *A01H 6/165* (2018.05)

(58) Field of Classification Search
USPC ..... Plt./318.6
CPC ..... A01H 6/165; A01H 5/02
See application file for complete search history.

*Primary Examiner* — Keith O. Robinson
(74) *Attorney, Agent, or Firm* — Cassandra Bright

(57) ABSTRACT

A new and distinct cultivar of *Impatiens* plant named 'DNGISLPROR' is disclosed, characterized by large, red-purple flowers. Plants are well-branched and sun-resistant. The new cultivar is an *Impatiens*, typically produced as an ornamental plant.

2 Drawing Sheets

Latin name of the genus and species: *Impatiens hawkeri.*
Cultivar denomination: 'DNGISLPROR'.

BACKGROUND OF THE INVENTION

The new *Impatiens* cultivar is a product of a planned breeding program conducted by the inventor, Gavriel Danziger. The objective of the breeding program was to produce useful new *Impatiens* varieties for ornamental horticultural production. The new cultivar is the result of a naturally occurring whole plant mutation of the unpatented, proprietary cultivar referred to as *Impatiens* 'BM-17-1000'. The new cultivar was discovered by the inventor in September of 2021 at a nursery in Moshav Mishmar Hashiva, Israel.

First asexual propagation of the new cultivar was performed by leaf cuttings in September of 2021, at the same nursery in Moshav Mishmar Hashiva, Israel.

SUMMARY OF THE INVENTION

The cultivar 'DNGISLPROR' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DNGISLPROR'. These characteristics in combination distinguish 'DNGISLPROR' as a new and distinct *Impatiens* cultivar:

1. Large, red-purple flowers.
2. Well branched plants.
3. Sun-resistance.

PARENT COMPARISON

Plants of 'DNGISLPROR' are similar in some horticultural characteristics to the seed parent. The new cultivar, however, differs in the following:

1. Flowers of the new cultivar are red-purple, while flowers of the seed parent are light salmon.
2. Flowers of the new cultivar are larger than flowers of the seed parent.
3. Flowers of the new cultivar are more abundant than flowers of the seed parent.

COMMERCIAL COMPARISONS

Plants of 'DNGISLPROR' are similar in some horticultural characteristics to the cultivar *Impatiens* 'DHAR319', U.S. Plant Pat. No. 23,943. The new cultivar, however, differs in the following:

1. Plants of the new cultivar are shorter than plants of this comparator.
2. Flower color of the new cultivar is lighter red-purple than the flower color of this comparator.
3. Plants of the new cultivar are more branched than plants of this comparator.

Plants of 'DNGISLPROR' are similar in some horticultural characteristics to the cultivar *Impatiens* 'DHARSCLVDR', U.S. Plant Pat. No. 27,673. The new cultivar, however, differs in the following:

1. Flower color of the new cultivar is darker red-purple than the flower color of this comparator.
2. Leaf color of the new cultivar is darker than the leaf color of this comparator.
3. Flowers of the new cultivar are more abundant than flowers of this comparator.

BRIEF DESCRIPTION OF THE PHOTOGRAPHS

Figure 1:
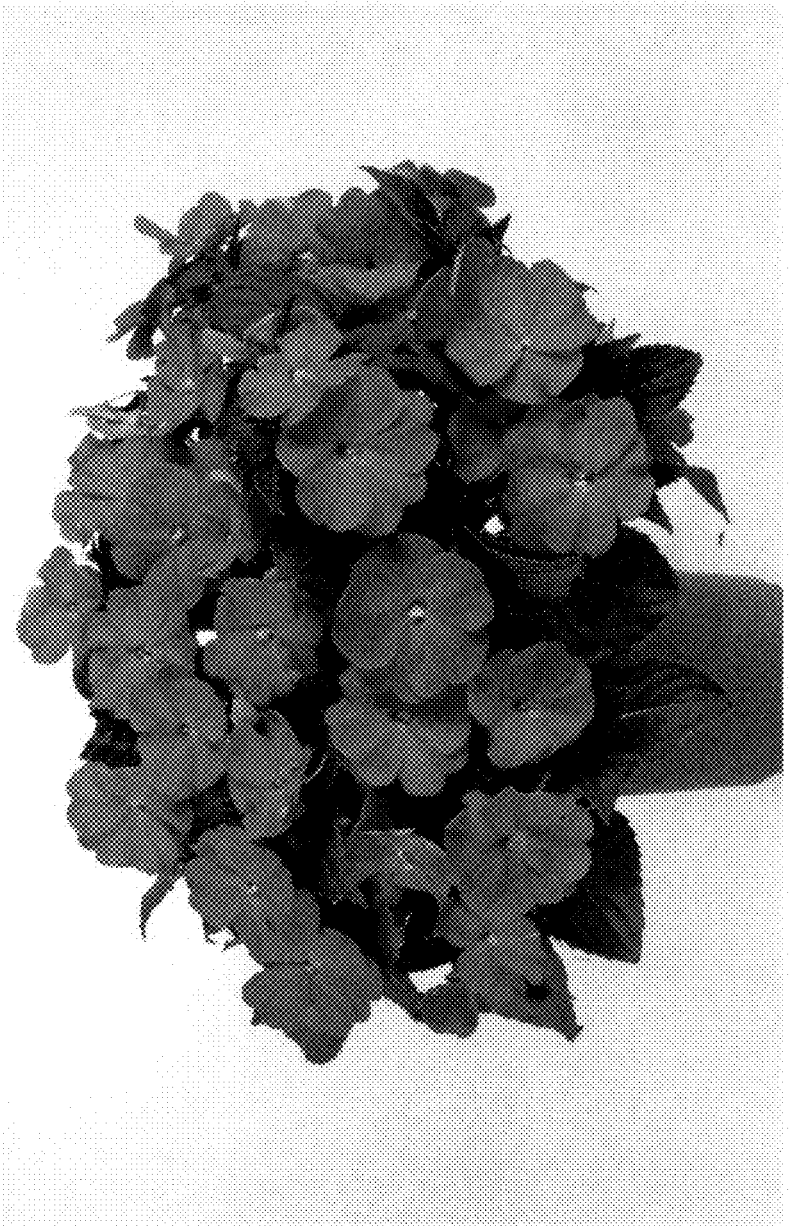

The accompanying photograph in FIG. 1 illustrates in full color a typical plant of 'DNGISLPROR' at about 13 weeks of age, grown in a 12 cm pot.

Figure 2:
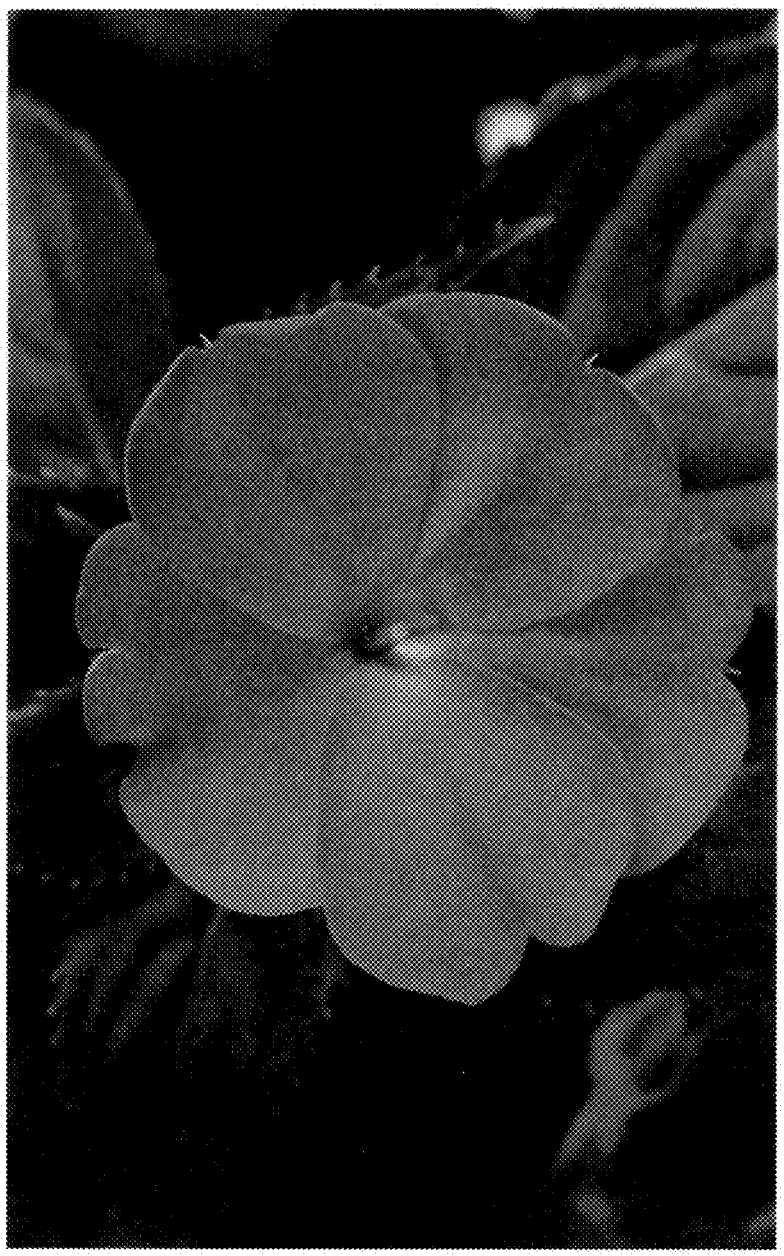

FIG. 2 illustrates a close-up view of a typical flower of the new cultivar.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Mini Colour Chart 2005 except where general terms of ordinary dictionary significance are used. The following observations and measurements describe 'DNGISLPROR' plants grown in a greenhouse in Moshav Mishmar Hashiva, Israel, under natural lighting. Measurements were taken during autumn. The growing temperature ranged from approximately 20° C. to 30° C. during the days, 15° C. to 25° C. during the nights. Measurements and numerical values represent averages of typical plant types.

Botanical classification: *Impatiens hawkeri* 'DNGISLPROR'.

PROPAGATION

Time to initiate rooting: 10 to 14 days in summer; 14 to 20 days in winter.

Age of plant described: 12 weeks from a rooted cutting.

PLANT

Growth habit: Mounded.
Pot size of plant described: 12 cm.
Height: 20 to 25 cm.
Plant spread: 30 to 35 cm.
Growth rate: Medium.
Branching characteristics: Well-branched.
Length of lateral branches: 15 to 20 cm.
Quantity of lateral branches: 5 to 8.
Characteristics of primary lateral branches:
- *Shape.*—Oval.
- *Diameter.*—1 cm.
- *Texture.*—Smooth.
- *Strength.*—Strong, very stable.
- *Color.*—RHS Yellow-Green 147C.

Internode length: 4 to 5 cm.

FOLIAGE

Leaf:
- *Arrangement.*—Alternate.
- *Quantity.*—Approximately 25 to 30 per branch.
- *Average length.*—7 cm.
- *Average width.*—3 to 4 cm.
- *Pubescence.*—None.
- *Shape.*—Lanceolate.
- *Apex.*—Apiculate.
- *Base.*—Acuminate.
- *Margin.*—Ciliate.
- *Texture.*—Smooth.
- *Aspect.*—45°.
- *Color.*—Young Foliage, Upper Side: RHS Green 138A. Young Foliage, Under Side: RHS Green 138B. Mature Foliage, Upper Side: RHS Green N137A. Mature Foliage, Under Side: RHS Green 138B.
- *Venation.*—Type: Pinnate. Color, Upper Side: RHS Green 138C. Color, Under Side: RHS Green 138D.

Petiole:
- *Length.*—0.5 to 1 cm.
- *Diameter.*—0.2 to 0.3 cm.
- *Color.*—RHS Green 138D.
- *Texture.*—Smooth.

FLOWER

Natural flowering season: Flowers at any day length. All year round in a greenhouse environment. Flowering is continuous from spring until fall in an outdoor garden.

Days to flowering from rooted cutting: 10 weeks.

Inflorescence and flower type and habit: Single flowers raised above the foliage. Corolla consists of 5 petals.

Rate of flower opening: 10 to 15 days from bud to fully opened flower.

Flower longevity on plant: 5 to 8 days.

Persistent or self-cleaning: Self-cleaning.

Bud:
- *Shape.*—Ovate.
- *Length.*—1.5 cm.
- *Diameter.*—1 cm.
- *Color.*—RHS Red-Purple N74D.

Flower size:
- *Diameter.*—7 cm.
- *Depth.*—4.5 cm.

Petals:
- *Arrangement.*—Overlapping.
- *Length.*—3.5 cm.
- *Width.*—3.5 cm.
- *Quantity.*—5.
- *Texture.*—Glabrous.
- *Apex.*—Heart-shaped.
- *Shape.*—Obcordate.
- *Margin.*—Entire.
- *Color.*—When Opening, Upper Surface: RHS Red-Purple N74A. When Opening, Lower Surface: RHS Red-Purple N74C. Fully Opened, Upper Surface: RHS Red-Purple N74A. Fully Opened, Lower Surface: RHS Red-Purple N74A.

Spurs:
- *Quantity.*—1 per flower.
- *Length.*—5 to 6 cm.
- *Diameter.*—0.1 cm.
- *Aspect.*—Spur curvature 40° to 45° from peduncle.
- *Color.*—RHS Purple-Pink 63C towards base; Green 140C at apex.

Sepals:
- *Quantity.*—2 per flower.
- *Shape.*—Oblong.
- *Length.*—1 cm.
- *Width.*—0.4 cm.
- *Apex.*—Caudate.
- *Base.*—Rounded.
- *Margin.*—Entire.
- *Color.*—RHS Yellow-Green 149C.

Peduncles:
- *Length.*—5 to 5.5 cm.
- *Width.*—0.2 cm.
- *Angle.*—About 45° to lateral branch.
- *Strength.*—Stable, flexible.

*Texture.*—Smooth.
*Color.*—RHS Yellow-Green 149C.
Fragrance: None.

REPRODUCTIVE ORGANS

Androecium:
Stamens:
*Quantity.*—5, with anthers that are more or less fused, forming a cap over the ovary.
Anthers:
*Shape.*—Oblong.
*Length.*—About 0.5 cm.
*Color.*—RHS White 159D.
*Pollen.*—None.
Gynoecium:
Pistil:
*Quantity.*—1.
*Length.*—0.5 cm.
*Style.*—Length: 0.5 cm. Color: RHS Yellow-Green 141B.
*Stigma.*—Shape: Round. Color: RHS Yellow-Green 142C. Ovary Color: RHS Yellow-Green 144D.

OTHER CHARACTERISTICS

Seeds and fruits: 5 to 10 seeds per fruit.
Disease/pest resistance: Neither resistance nor susceptibility of diseases common to *Impatiens* observed.
Temperature tolerance: Tolerant at 30° C.and 5° C. Grows best at 10° C. to 28° C.

What is claimed is:

1. A new and distinct cultivar of *Impatiens* plant named 'DNGISLPROR' as herein illustrated and described.

* * * * *